US006322980B1

(12) United States Patent
Singh (10) Patent No.: US 6,322,980 B1
(45) Date of Patent: *Nov. 27, 2001

(54) SINGLE NUCLEOTIDE DETECTION USING DEGRADATION OF A FLUORESCENT SEQUENCE

(75) Inventor: Sharat Singh, San Jose, CA (US)

(73) Assignee: Aclara Biosciences, Inc., Hayward, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 18 days.

(21) Appl. No.: 09/303,029

(22) Filed: Apr. 30, 1999

(51) Int. Cl.⁷ ............... C12Q 1/68; C12P 19/34; C07H 21/02; C07H 21/04; B01D 57/02
(52) U.S. Cl. ............... 435/6; 435/91.2; 536/23.1; 536/24.3; 536/25.32; 204/450
(58) Field of Search ............ 435/91.2, 6; 536/23.1, 536/24.3, 25.32; 204/450

(56) References Cited

U.S. PATENT DOCUMENTS

| 5,470,705 | 11/1995 | Grossman et al. ............ 435/6 |
| 5,552,028 | 9/1996 | Madabhushi et al. ......... 204/451 |
| 5,565,324 | 10/1996 | Still et al. ................. 435/6 |
| 5,567,292 | 10/1996 | Madabhushi et al. ......... 204/451 |
| 5,580,732 | 12/1996 | Grossman et al. ............ 435/6 |
| 5,624,800 | 4/1997 | Grossman et al. ............ 435/6 |
| 5,703,222 | 12/1997 | Grossman et al. .......... 536/24.3 |
| 5,807,682 | 9/1998 | Grossman et al. ............ 435/6 |
| 5,874,213 * | 2/1999 | Cummins et al. ............. 435/6 |
| 5,916,426 | 6/1999 | Madabhushi et al. ......... 204/451 |
| 5,989,871 | 11/1999 | Grossman et al. .......... 435/91.1 |

OTHER PUBLICATIONS

Brenner and Lerner (1992) *PNAS* 89:5381–83.
Fan (Oct. 6–8, 1997) IBC, Annapolis MD.
Hacia (1996) *Nat. Genet.* 14:441–47.
Haff (1997) *Nucleic Acids Res.* 25:3749–50.
Holland (1991) *Proc. Natl. Acad. Sci. USA* 88:7276–80.
Lee (1993) *Nucleic Acid Research* 21:16 3761–66.
Marino (1996) *Electrophoresis* 17:1499–04.
Pastinen (1996) *Clin. Chem.* 42:1391–97.
Ross (1997) *Anal. Chem.* 69:4197–4202.
Still et al. (1996) *Accounts of Chem. Res.* 29:155–63.
White (Dec. 1996) *Tibtech* 14(12): 478–83.

* cited by examiner

Primary Examiner—Stephanie Zitomer
Assistant Examiner—Joyce Tung (57) ABSTRACT

Methods and compositions are provided for detecting single nucleotide polymorphisms using a pair of oligonucleotides, a primer and a snp detection sequence, where the snp detection sequence hybridizes to the target DNA downstream from the primer and in the direction of primer extension. The snp detection sequence is characterized by having a nucleotide complementary to the snp and adjacent nucleotide complementary to adjacent nucleotides in the target and an electophoretic tag bonded to the 5'-nucleotide. The pair of oligonucleotides is combined with the target DNA under primer extension conditions, where the polymerase has 5'-3' exonuclease activity. When the snp is present, the electrophoretic tag is released from the snp detection sequence, and can be detected by electrophoresis as indicative of the presence of the snp in the target DNA.

12 Claims, 5 Drawing Sheets

Fluorescent Dyes

A.

CCA GCA ACC AAT GAT GCC CGT T-TAMARA-3'
CA GCA ACC ATT GAT GCC CGT T-TAMARA-3'

CCA GCA AGC ACT GAT GCC TGT T-TAMARA-3'
CA GCA AGC ACT GAT GCC TGT T-TAMARA-3'

B.

|  | Absorbance Maxima | Emission Maxima |
|---|---|---|
| Fluorescein | 494 nm | 525 nm |
| Tetrachloro Fluorescein | 521 nm | 536 nm |
| TAMRA | 565 nm | 580 nm |

C.

Cleaved Fragments:

SEQUENCE LISTING

<160> NUMBER OF SEQ ID NOS: 7

<210> SEQ ID NO 1
<211> LENGTH: 16
<212> TYPE: DNA
<213> ORGANISM: Artificial
<220> FEATURE:
<223> OTHER INFORMATION: artificial sequence based on human genome

```
<400> SEQUENCE: 1
tcaccacatc ccagtg                                                    16

<210> SEQ ID NO 2
<211> LENGTH: 16
<212> TYPE: DNA
<213> ORGANISM: Artificial
<220> FEATURE:
<223> OTHER INFORMATION: artificial sequence based on human genome

<400> SEQUENCE: 2
gagggaggtt tggctg                                                    16

<210> SEQ ID NO 3
<211> LENGTH: 22
<212> TYPE: DNA
<213> ORGANISM: Artificial
<220> FEATURE:
<223> OTHER INFORMATION: artificial sequence based on human genome
<221> NAME/KEY: 5'clip
<222> LOCATION: (1)..(1)
<223> OTHER INFORMATION: 5' nucleotide linked to tetrachlorofluorescein
<221> NAME/KEY: 3'clip
<222> LOCATION: (22)..(22)
<223> OTHER INFORMATION: 3' nucleotide linked to tetramethyl rhodamine

<400> SEQUENCE: 3
ccagcaacca atgatgcccg tt                                             22

<210> SEQ ID NO 4
<211> LENGTH: 22
<212> TYPE: DNA
<213> ORGANISM: Artificial
<220> FEATURE:
<223> OTHER INFORMATION: artificial sequence based on human genome
<221> NAME/KEY: 5'clip
<222> LOCATION: (1)..(1)
<223> OTHER INFORMATION: 5' nucleotide linked to fluorescein
<221> NAME/KEY: 3'clip
<222> LOCATION: (22)..(22)
<223> OTHER INFORMATION: 3' nucleotide linked to tetramethyl rhodamine

<400> SEQUENCE: 4
ccagcaagca ctgatgcctg tt                                             22

<210> SEQ ID NO 5
<211> LENGTH: 4
<212> TYPE: PRT
<213> ORGANISM: Artificial
<220> FEATURE:
<223> OTHER INFORMATION: strictly artificial peptide with specific ratio
      of lysines and alanines to achieve different charge/mass
      characteristic

<400> SEQUENCE: 5

Lys Lys Ala Ala
1

<210> SEQ ID NO 6
<211> LENGTH: 4
<212> TYPE: PRT
<213> ORGANISM: Artificial
<220> FEATURE:
<223> OTHER INFORMATION: strictly artificial peptide with specific ratio
      of lysines and alanines to achieve different mass/charge
      characteristic

<400> SEQUENCE: 6
```

```
-continued

Lys Lys Lys Ala
1

<210> SEQ ID NO 7
<211> LENGTH: 4
<212> TYPE: PRT
<213> ORGANISM: Artificial
<220> FEATURE:
<223> OTHER INFORMATION: strictly artificial peptide sequence with
      specific ratios of lysines and alanines to achieve different
      mass/charge characteristics

<400> SEQUENCE: 7

Lys Lys Lys Lys
```

SINGLE NUCLEOTIDE DETECTION USING DEGRADATION OF A FLUORESCENT SEQUENCE

FIELD OF THE INVENTION

The field of this invention is the detection of single nucleotide polymorphisms.

BACKGROUND OF THE INVENTION

As the human genome is elucidated, there is, and will continue to be comparisons of the sequences of different individuals. It is believed that there will be about one polymorphism per 1,000 bases, so that one may anticipate that there will be a extensive number of differences between individuals. By single nucleotide polymorphism (snp's) is intended that there will be a prevalent nucleotide at the site, with one or more of the remaining bases being present in a substantially smaller percent of the population.

For the most part, the snp's will be in non-conding regions, primarily between genes, but will also be present in exons and introns. In addition, the great proporton of the snp's will not affect the phenotype of the individual, but will clearly effect the genotype. The snp's have a number of properties of interest. Since the snp's will be inherited, individual snp's and/or snp patterns may be related to genetic defects, such as deletions, insertions and mutations, involving one or more bases in genes. Rather than isolating and sequencing the target gene, it will be sufficient to identify the snp's involved.

In addition, the snp's may be used in forensic medicine to identify individuals. While other genetic markers are available, the large number of snp's and their extensive distribution in the chromosomes, make the snp's an attractive target. Also, by determining a plurality of snp's associated with a specific phenotype, one may use the snp pattern as an indication of the phenotype, rather than requiring a determination of the genes associated wit the phenotype.

The need to identify a large number of bases distributed over potentially centimorgans of DNA offers a major challenge. Any method should be accurate, reasonably economical in limiting the amount of reagents required and providing for a single assay, which allows for differentiation of the different snp's.

BRIEF DESCRIPTION OF THE RELATED ART

Holland (*Proc. Natl. Acad. Sci. USA* (1991):88:7276) discloses that the exonuclease activity of the thermostable enzyme Thermus aquaticus DNA polymerase in PCR amplification to generate specific detectable signal concomitantly with amplification.

The TAQMAN assay is discussed by Lee in *Nucleic Acid Research* (1993) 21:16 3761).

White (Trends Biotechnology (1996) 14(12); 478–483) discusses the problems of multiplexing in the TAQMAN assay.

Marino, *Electrophoresis* (1996) 17:1499 desribes low-strigency-sequence specific PCR (LSSP-PCR). A PCR amplified sequence is subjected to single primer amplification under conditions of low stringency to produce a range of different length amplicons. Different patterns are obtained when there are differences in sequence. The patterns are unique to an individual and of possible value for identity testing.

Single strand conformation a polymorphism (SSCP) yields similar results. In this method the PCR amplified DNA is denatured and sequence dependent conformations of the single strands are detected by their differing rates of migration during gel electrophoresis. As with LSSP-PCR above, different patterns are obtained that signal differences in sequence. However, neither LSSP-PCR nor SSCP gives specific sequence information and both depend on the questionable assumption that any base that is changed in a sequence will give rise to a conformational change that can be detected.

Pastinen, *Clin. Chem,* (1996) 42:1391 amplifies the target DNA and immobilizes the amplicons. Multiple primers are then allowed to hybridize to sites 3' and contiguous to an SNP site of interest. Each primer has a different size that serves as a code. The hybridized primers are extended by one base using a fluorescently labeled dideoxynucleoside triphosphate. The size of each of the fluorescent products that is produced, determined by gel electrophoresis, indicates the sequence and, thus, the location of the SNP. The identity of the base at the SNP site is defined by the triphosphate that is used. A similar approach is taken by Haff, *Nucleic Acids Res.* (1997) 25:3749 except that the sizing is carried out by mass spectroscopy and thus avoids the need for a label. However, both method have the serious limitation that screening for a large number of sites will require large, very pure primers that can have troublesome secondary structures and be very expensive to synthesize.

Hacia, *Nat. Genet.* (1996) 14:441 uses a high density array of oligonucleotides. Labeled DNA samples were allowed to bind to 96,600 20-base oligonucleotides and the binding patterns produced from different individuals were compared. The method is attractive in that SNP's can be directly identified but the cost of the arrays is high.

Fan (Oct. 6–8, 1997, IBC, Annapolis Md.) has reported results of a large scale screening of human sequence-tagged sites. The accuracy of single nucleotide polymorphism screening was determined by conventional ABI resequencing.

Allele specific oligonucleotide hybridization along with mass spectroscopy has been discussed by Ross in *Anal. Chem.* (1997) 69:4197.

Brenner and Lener, *PNAS* (1992) 89:5381, suggested that compounds prepared by combinatorial synthesis can each be labeled with a characteristic DNA sequence. If a given compound proves of interest, the corresponding DNA label is amplified by PCR and sequence thereby identifying the compound.

W. Clark Still, in U.S. Pat. No. 5,565,324 and in Accounts of Chem. Res., (1996) 29:155, uses a releasable mixture of halocarbons on beads to code for a specific compound on the bead that is produced during synthesis of a combinatorial library. Beads bearing a compound of interest are treated to release the coding molecules and the mix is analyzed by gas chromatography with flame ionization detection.

SUMMARY OF THE INVENTION

Snp's are detected by employing a combination of a primer and fluorescent snp detector sequence in the presence of primer extension reagents, where the polymerase includes 5'-3' exonuclease activity. The fluorescent snp detector sequence has at least one nucleotide which is substituted with an electrophoretic tag. One combines the target DNA, which will usually have been processed, with the primer extension reagents and at least one oligonucleotide pair for each snp of interest under conditions for primer extension. After sufficient time for primer extension to occur with degradation of detector sequences bound to target DNA, the electrophoretic tags, which are fluorescent or are made fluorescent, are separated and detected. By having a different electrophoretic tag for each snp, with each electrophoretic tag having a different electrophoretic mobility, one can readily determine the snp's which are present in the target DNA.

Electrophoretic tags are also provided for use in the snp detection method.

BRIEF DESCRIPTION OF THE DRAWINGS

FIGS. 1A, B and C depict the specific sequences of the snp detection sequences for the two alleles, the optical characteristics of the fluorescent dyes, and the cleaved fragments from the snp detection sequences, respectively.

FIGS. 2A and B depict the CE separation of reaction products of Allele 1 after 0 and 40 cycles CE instrument: Beckman P/ACE/5000 with LIF detection. BGE: 2.5% LLD 30, 7M urea, 1×TBE. Capillary. 100 μm i.d., 375;μm o.d., Lc=27 cm, Ld=6.9 cm. Detection; $\lambda_{EX}$=488 nm, $\lambda_{em}$=520 mn. Injection: 5s at 2.0 kV. Field strength: 100V/cm at rt. Peaks: P=unreacted snp detection sequence, P'=snp detection sequence product.

FIGS. 3A and B depict the CE separation of the reaction products of Allele 2 after 0 and 40 cycles. Experimental conditions are the same as FIG. 2, except for BGE composition; 2.% LDD30, 1×TBE;

DESCRIPTION OF THE SPECIFIC EMBODIMENTS

One, usually a plurality, of snp's, is simultaneously determined by combining target DNA with one or a plurality, respectively, pair of reagents under conditions of primer extension. The pair of reagents is a prier which binds to target DNA and a fluorescent snp detection sequence, which binds to the site of the snp and has a fluorescent electrophoretic tag, usually at its 5'-end and the base complementary to the snp, usually at other than a terminus of the snp detection sequence. The conditions of primer extension employ a polymerase having 5'-3' exonuclease activity, dNTP's and auxiliary regents to permit efficient primer extension The primer extension is performed, whereby detector sequences bound to the target DNA are degraded with release of the electrophoretic tag. By having each snp be associated with its own electrophoretic tag, one can determine the snp's which are present in the target DNA for which pairs of reagents have been provided.

The pairs of reagents are DNA sequences which are related to a snp site. The primer binds to the target DNA upstream from the snp site in the direction of extension. The fluorescent detector sequence binds downstream from the primer in the direction of extension and binds to a sequence which includes the snp. The primer sequence will usually be at least about 12 bases long, more usually at least 18 bases long and usually fewer than 100 bases, more usually fewer than 60 bases. The primer will be chosen to bind substantially uniquely to a target sequence under the conditions of primer extension, so that the sequence will normally be one that is conserved or the primer is long enough to bind in the presence of a few mismatches, usually fewer than about 10% mismatches. By knowing the sequence which is upstream from the snp of interest, one may select a sequence which has a high G-C ratio, so as to have a high binding affinity for the target sequence. In addition, the primer should bind reasonably close to the snp, usually not more than about 200 bases away, more usually not more than about 100 bases away, and preferably within about 50 bases. Since the farther away the primer is from the snp, the greater amount of dNTP's which will be expended, there will usually be no advantage in having a significant distance between the primer and the snp detection sequence. Generally, the primer will be at least about 5 bases away from the snp.

The fluorescence snp detection sequence will be chosen to bind to the target sequence comprising the snp. The length of the snp detector sequence is in part related to the length and binding affinity of the primer. The two sequences act together to ensure that the pair of reagents bind to the proper target sequence. The greater the fidelity of binding of one member of the pair, the less fidelity that is required for the other member of the pair. Since the observed signal will be dependent upon both members of the pair being present, each member serves as a check on the other member for production of the signal. However, since except for the cost, it is relatively easy to make reasonably long oligonucleotides, usually both members of the pair will uniquely hybridize to their respective target sequences. Therefore, the length of the snp detector sequence will come within the parameters indicated for the primer, but the total number of bases for the two pair members will be at least 36, more usually at least about 40.

Each snp detection sequence will have at least one nucleotide modified with an electrophoretic tag, which is fluorescent or can be subsequently made fluorescent. Usually, the modified nucleotide will be at the 5'-end of the sequence, but the modified nucleotide may be less desirably anywhere in the sequence. Since the determination is based on the degradation of the snp detector sequence, having the modified nucleotide at the end ensures that if degradation occurs, the electrophoretic tag will be released. Since nucleases may clip at other than the terminal phosphate link, it is desirable to prevent cleavage at other than the terminal phosphate link. In this way one avoids the confusion of having the same electrophoretic tag joined to different numbers of nucleotides after cleavage. Cleavage at the terminal phosphate can be relatively assured by using a linker at the penultimate nucleoside to the next nucleoside in the 5'-3' direction, which is not cleaved by the nuclease. For example, one may use a thiophosphate, phosphinate, phosphoramidate, or a linker other than a phosphorous acid derivative. If desired all of the linkers other than the ultimate linker may be resistant to nuclease hydrolysis.

The complementary base to the snp may be anywhere in the detector sequence, desirably at other than the terminal nucleoside to enhance the fidelity of binding, preferably central to the nucleotide sequence. The snp detector sequence will be designed to include adjacent nucleotides, which provide the desired affinity for the hybridization conditions. The snp detection sequence may be synthesized by any convenient means, such as described in Matthews, et al,, Anal Biochem. (1988) 169:1–25 Keller, et al., "DNA Probes," $2^{nd}$ edition (1993) Stockton Press, New York, N.Y.; and Wetmur, Critical Reviews in Biochemistry and Molecular Biology (1991) 26:227–259.

The electrophoretic tag will be one which is fluorescent or can be made so by functionalization. The electrophoretic tags will be differentiated by their mass/charge ratio, to provide different mobilities for each electrophoretic tag.

Therefore, the tags will be amenable to electrophoretic separation and detection, although other methods of differentiating the tags may also find use. The electrophoretic tag may be joined to any convenient site on the nucleotide, without interfering with the snp detector sequence and without interfering with the hydrolysis of the phosphate linkage to release the electrophoretic tag. Thus, the tag may be bound to a site on the base, either an annular carbon atom or a hydroxyl or amino substituent. The electrophoretic tag may be linked by a stable bond or one which may be cleavable, thermally, photolytically or chemically. There is an interest in cleaving the electrophoretic tag from the nucleotide where the snp detector sequence results in significant cleavage at other than the 5'-phosphate link, resulting in di- and higher oligonucleotides and this family of products interferes with the separation and detection of the electrophoretic tags. However, rather than requiring an additional step it identification of the tags by releasing them from the base to which they are attached, one can modify snp detection sequence to minimize obtaining cleavage at other than the ultimate linker.

If present, the nature of the releasable link may be varied widely. Numerous linkages are available, which are thermally, photolytically or chemically labile. See, for example, U.S. Pat. No. 5,721,099. Where detachment of the product is desired, there are numerous functionalities and reactants, which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ beta-elimination, where a mild base may serve to release the product. Acetals, including the thio analogs thereof, may be employed, where mild acid, particularly in the presence of a capturing carbonyl compound, may serve. By combining formaldehyde, HCl and an alcohol moiety, an $\alpha$-chloroether is formed. This may then be coupled with an hydroxy functionality to form the acetal. Various photolabile linkages may be employed, such as o-nitrobenzyl, 7nitroindanyl, 2-nitrobenzhydryl ethers or esters, etc.

For a list of cleavable linkages, see, for example, Greene and Wuts, Protective Groups in Organic Synthesis, $2^{nd}$ ed. Wiley, 1991. The versatility of the various systems that have been developed allows for broad variation in the conditions for attachment of the electrophoretic tag entities.

Various functionalities for cleavage are illustrated by: silyl groups being cleaved with fluoride, oxidation, acid, bromine or chlorine; o-nitrobenzyl with light; catechols with cerium salts; olefins with ozone, permanganate or osmium tetroxide; furans with oxygen or bromine in methanol; tertiary alcohols with acid; ketals and acetals with acid; $\alpha$- and $\beta$-substituted ethers and esters with base, where the substituent is an electron withdrawing group, e.g., sulfone, sulfoxide, ketone, etc., and the like.

The electrophoretic tags comprise a linker, which provides the linkage between the base and the fluorescent molecule or a functionality which may be used for linking to a fluorescent molecule. By having different functionalities which may be individually bonded to a fluorescent molecule, one enhances the opportunity for diversity of the electrophoretic tags. Using different fluorescers for joining to the different functionalities, the different fluorescers can provide differences in light emission and mass/charge ratios for the electrophoretic tags.

For the most part, the links will be oligomers, where the monomers may differ as to mass and charge. For convenience and economy, monomers will generally be commercially available, but if desired, they may be originally synthesized. Monomers which are commercially available and readily lend themselves to oligomerization include amino acids, both natural and synthetic, nucleotides, both natural and synthetic, and monosaccharides, both natural and synthetic, while other monomers include hydroxyacids, where the acids may be organic or inorganic, e.g. carboxylic, phosphoric, boric, sulfonic, etc., and amino acids, where the acid is inorganic, and the like The monomers may be neutral, negatively charged or positively charged. Normally, the charges of the monomers in the links will be the same, so that in referring to the mass/charge ratio, it will be related to the same charge. Where the fluorescer has a different charge from the linker, is will be treated as if the number of charges are reduced by the number of charges on the linker. For amino acids, the positive charges may be obtained from lysine, arginine and histidine, while the negative charges may be obtained from aspartic and glutamic acid. For nucleotides, the charges will be obtained form the phosphate and any substituent that may be present or introduced onto the base. For sugars, silic acid, uric acids of the various sugars, or substituted sugars may be employed. As appropriate, one may have two or more reaction mixtures with different multiple snp determinations in each reaction mixture.

For the most part, the linker may be a bond where the fluorescer is directly bonded to the nucleoside or may be a link of from 1 to 500 or more, usually 2 to 300 atoms in the chain. The total number of atoms in the chain will depend to a substantial degree on the diversity required to recognize all the snp's to be determined. The chain of the link for the most part will be comprised of carbon, nitrogen, oxygen, phosphorous, boron, and sulfur. Various substituents may be present on the linker, which may be naturally present as part of the naturally occurring monomer or introduced by synthesis. Functionalities which may be present in the chain include amides and esters, carboxylate, phosphate, sulfate, boronate, etc. and thio derivatives thereof, ethers, thioethers, disulfides, etc. The side chains include amines, ammonium salts, hydroxyl groups, including phenolic groups, amides and esters and thio analogs thereof, of organic and inorganic acids, e.g., carboxyl, phosphates, sulfate, boronate, etc., heterocycles, particularly nitrogen heterocycles, such as the nucleoside bases and the amino acid side chains, such as imidazole and indole, thioethers, thiols, or other groups of interest to change the mobility of the electrophoretic tag. The linker may be a homooligomer or a heterooligomer, having different monomers of the same or different chemical characteristics, e.g., nucleotides and amino acids.

The linker may joined in any convenient manner to the base of the nucleoside. Various functionalities which may be used include alkylamine, amidine, thioamide, ether, urea, thiourea, guarndine, azo, thioether and carboxylate, sulfonate, and phosphate esters, amides and thioesters Besides the nature of the linker, as already indicated, diversity can be achieved by the chemical and optical characteristics of the fluoreser, the use of energy transfer complexes, variation in the chemical nature of the linker, which affects mobility, such as folding, interaction with the solvent and ions in the solvent and the like. As already suggested, the linker will usually be an oligomer, where the linker may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group so that there is a unique functionality which may be differentially functionalized. By using protective groups, one can distinguish a side chain functionality from a terminal amino acid functionality. Also, by appropriate design, one may provide for preferential reaction between the same functonalities present at different sites on the linking group. Whether one uses synthesis or cloning for preparation of oligopeptides, will to a substantial degree depend on the length of the linker.

The electrophoretic tag, which is detected, will comprise the linker and a fluorescer and optionally the nucleotide of the snp detection sequence. Generally, the electrophoretic tag will have a charge/mass ratio in the range of about −0.0101 to 0.1, usually in the range of about −0.001 to about 0.5. Mobility is $q/M^{2/3}$, where q is the charge on the molecule and M is the mass of the molecule. Desirably, for accurate discimination, the difference in mobility under the conditions of the determination between the closes electrophoretic labels will usually be at least sufficient to individually detect the electrophoric retic tags, generally being at least about 0.05, more usually at least about 0.1.

If desired, the snp detection sequence may have a combination of a quencher and a fluorescer. In this instance, the fluorescer would be in proximity to the nucleoside to which the linker is bonded, as well as the quencher, so that in the primer extension mixture, fluorescence from fluorescer bound to the snp detection sequence would be quenched. As the reaction proceeds and fluorescer is released from the snp detection sequence and, therefore, removed from the quencher, it would then be capable of fluorescence. By monitoring the primer extension mixture for fluorescence, one would be able to determine when there would probably be a sufficient amount of individual electrophoretic tags to provide a detectable signal for analysis. In this way, one could save time and reagent by terminating the primer extension reaction at the appropriate time. There are many quenchers which are not fluorescers, so as to minimize fluorescent background from the snp detection sequence. Alternatively, one could take small aliquots and monitor the reaction for observable electrophoretic tags.

The extension reaction is performed by bringing together the necessary combination of reagents and subjecting the mixture to conditions for carrying out the desired primer extension, usually involving amplification. Such conditions depend on the nature of the extension, e.g., PCR, single primer amplification, LCR, NASBA, 3SR and so forth, where the enzyme which is used for the extension has 5'-3' nuclease activity. The extension reaction may be carried out as to both strands or as to only a single strand. Where pairs of primer and snp detection sequence are used for both strand, conveniently, the electrophoretic tag will be the same, but the bases will be different. In this situation, one may wish to have a cleavable linkage to the base, so that for the same snp, one would obtain the same electrophoretic tag. Alternatively, if the number of snp's to be determined is not too high, one could use different electrophoretic tags for each of the strands. Usually, the reaction will be carried out by using amplifying conditions, so as to provide an amplified signal for each snp. Amplification conditions normally employ thermal cycling, where after the primer extension and release of electrophoretic tags associated with snps' which are present, the mixture is heated to denature the double-stranded DNA, cooled, where the primer and snp detection sequence an rehybiridize and the extension repeated.

The nucleoside triphosphates employed as reagents in an amplification reaction include deoxyribonucleoside triphosphates such as the four common deoxyribonucleoside triphosphates dATP, dCTP, dGTP and dTTP. The term "nucleoside triphosphates" also includes derivatives and analogs thereof, which are exemplified by these derivatives that are recognized and polymerized in a similar manner to the underivatized nucleoside triphosphates.

The nucleotide polymerase employed is a catalyst usually an enzyme, for forming an extension of an oligonucleotide primer along a polynucleotide such as a DNA template, where the extension is complementary thereto. The nucleotide polymerase is a template dependent polynucleotide polymerase and utilizes nucleoside, triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I,II, or III) T4 DNA polymerase, T7 DNA polymerase, Vent DNA polymerase, Pfu DNA polymerase, Taq DNA polymerase, and the like. Polymerase enzymes may be derived from any source, such as eukaryotic or prokaryotic cells, bacteria such as *E. coli,* plants, animals, virus, thermophilic bacteria, genetically modified enzymes, and so forth.

The conditions for the various amplification procedures are well known to those skilled in the art. In a number of amplification procedures thermal cycling conditions as discussed above are employed to amplify the polynucleotide. The combination of reagents is subjected to conditions under which the oligonucleotide pricer hybrdizes to the priming sequence of, and is extended along, the corresponding polynucleotide. The exact temperatures can be varied depending on the salt concentration, pH, solvents red, length of and composition of the target polynucleotide sequence and the oligonucleotide primers.

Thermal cycling conditions are employed for conducting an amplificatiion involving temperate or thermal cycling and primer extension such as in PCR or single primer amplification, and the like. The pH and the temperature are selected so as to cause, either simultaneously or sequentially, dissociation of any internally hybrdized sequences, hybridization or annealing of the oligonucleotide primer and snp detection sequence with the target polynucleotide sequence, extension of the PHMEY release of the electrophoretic tag from snp detection sequence bound to the target polynucleotide sequence and dissociation of the extended primer and residual snp detection sequences. This usually involves cycling the reaction medium among two or more temperatures. In conducting such a method, the medium is cycled between two to three temperatures, The temperatures for thermal cycling generally range from about 50° C. to 100° C., more usually, from about 60° C. to 95° C. Relatively low temperatures of from about 30° C. to about 65° C. can be employed for the extension steps, while denaturation and hybridization can be carried out a a temperature of from about 50° C. to about 105° C. The reaction medium is initially at about 20° C. to about 45° C., preferably, about 25° C. to about 35° C. Relatively low temperatures of from about 50° C. to about 80° C., preferably, 50° C. to about 60° C., are employed for the hybridization or "annealing steps, while denaturation is carried out at a temperature of from about 80° C. to about 100° C., preferably, 90° C. to about 95° C., and extension is carried out at a temperature of from about 70° C. to about 80° C., usually about 72° C. to about 74° C. The duration of each cycle may vary and is usually about 1 to 120 seconds, preferably, about 5 to 60 seconds for the denaturantion steps, and usually about 1 to 15 seconds, preferably, about 1 to 5 seconds, for the extension steps. It is to be understood that the actual temperature and duration of the cycles employed are dependent on the particular amplification conducted and are well within the knowledge of those skilled in the art.

Generally, an aqueous medium is employee. Other polar cosolvents may also be employed, usually oxygenated organic solvents of from 1–6, more usually from 1–4, carbon atoms, including alcohols, ethers, formamide and the like. Usually, these cosolvents, if used, are present in less than about 70 weight percent more usually in less than about 30 weight percent.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. The medium may also contain materials required for enzyme activity such as a divalent metal ion (usually magnesium).

The selection of the snp detection sequence will affect the stringency employed during the primer extension, particularly at the stage of hybridization. Since in a substantial number of samples, the DNA will he heterozygous for snps rather than homozygous, one does not wish to have false positives, where the snp detection sequence may bond to the sequence comprising the prevalent nucleotide, as well as the sequence comprising the snp. Where the DNA sample is homozygous for the prevalent sequence, it is also important that the snp detection sequence does not bind to give a false positive. Therefore, the difference in $T_m$ between the snp containing sequence and the wild-type sequence will usually be at least about 3° C., more usually at least about 5° C., under the conditions of the primer extension.

Various ancillary materials will frequency be employed in the methods in accordance with the present invention. For example, in addition to buffers and salts, the medium may also comprise stabilizers for the medium and the reactive components. Frequently, the medium may also include proteins such as albumins, quaternary ammonium salts, polycations such as spine, surfactants, particularly non-ionic surfactants, binding enhancers, e.g., polyalkylene glycols, or the like.

The reaction is conducted for a time sufficient to produce the desired number of copies of each of the polynucleotides suspected of being present as discussed below. Generally, the time period for conducting the entire method will be from about 10 to 200 minutes. As mentioned above, it is usually desirable to minimize the time period.

The concentration of the nucleotide polymerase is usually determined empirically. Preferably, a concentration is used that is sufficient such that the amplification is robust. The primary limiting factor generally is the cost of the reagent. Such enyzmes include Pfu DNA polymerase (native and recombinant) from Stratagene, La Jolla, Calif., UITma DNA polymerase from Perkin Elmer, Foster City, Calif., rBst DNA polymerase from Epicentre Technologies, Madison, Wis., and Vent DNA polymerase from New England Biolabs, Beverly, Mass., Tli DNA polymerase from Proega Corp., Madison, Wis., and Pwo DNA polymerase from Boehringer Mannheim, Indianapolis; Ind., and the like.

The initial concentration of each of the polynucleotides containing the respective target snps can be as low as about 50 picograms per microliter in a sample. After amplification the concentration of each polynucleotide should be at east about 10 picomolar, generally in the range of about 10 picomolar to about 10 nanomoler, usually from about 10 to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$ M. In general, the reagents for the reaction are provided in amounts to achieve extension of the oligonucleotide primers The concentration of the oligonucleotide primer(s) will be 1 to about 20 micromolar and is usually about 1 to about 10 micro molar, preferably, about 1 to about 4 micromolar, for a sample size that is about 10 femtomolar. Preferably, the concentration of the oligonucleotide primer(s) is substantially in excess over, preferably at least about $10^7$ to about $10^{10}$ times greater tan, more preferably, at least about $10^9$ times greater than, the concentration of the corresponding target polynucleotides.

The amount of the oligonucleotide pairs will be 10 to about 500 nanomolar and is usually about 50 to about 200 nanomolar for a sample size that is about 10 femtomolar (10 femtograms per microliter). Preferably, the concentration of the oligonucleotide pairs is substantially in excess over, preferably at least $10^7$ times greater than, more preferably, at least about $10^8$ times greater than, the concentration of each of the target polynucleotides.

The concentration of the nucleoside triphosphates in the medium can vary widely; preferably, these reagents are present in an excess amount. The nucleoside triphosphates are usually present in about 10 micro molar to about 1 millimolar, preferably, about 20 to about 400 micromolar.

The order of combining of the various regeants to form the combination may vary. Usually, the sample containing the polynucleotides is combined with a pre-prepared combination of nucleoside triphosphates and nucleotide polymerase. The oligonucleotide primers and the snp detection sequences may be included in the prepared combination or may be added subsequently. However, simultaneous addition of all of the above, as well as other step-wise or sequential orders of addition, may be employed provided that all of the reagents described above are combined prior to the start of the reactions. The oligonucleotide pairs are added to the combination of the reagents at or prior to intiation of the primer extension reaction and may be replenished from time-to-time during the primer extension reaction.

After completion of the primer extension reaction, either by monitoring the change in fluorescence as described above or taking aliquots and assaying for total free electrophoretic tags, the mixture may now be analyzed. Depending on the instrument, today from one to four different fluoxescers activated by the same light source and emitting at different detectable labels may be used. With improvements, five or more different fluorescers will be available, where an additional light source may be required.

In those instances where a fluorescent tag is not present on the electrophoretic tag bound to the snp detection sequence, the mixture may be added to functionalized fluorescent tags to label the electrophoretic tag with a fluorescer. For example, where a thiol group is present, the fluorescer could have an activated ethylene, such as maleic acid to form the thioether, or a disulfide to undergo displacement to form a new disulfide between the linker and the fluorophor. For hydroxyl groups, one could use as activated halogen or pseudohalogen for forming an ether, such as an α-haloketone. For carboxyl groups, carbodiimide and appropriate amines or alcohols would form amides and esters, respectively. For an amine, one could use activated carboxylic acids, aldehydes under reducing conditions, activated halogen or pseudohalogen, etc. When synthesizing oligopeptides, protective groups are used. These could be retained while the fluorescent moiety is attached to an available functionality on the oligopeptide. The syntheses and reactions are conventional and performed in accordance with known procedures.

The presence of each of the cleaved electraphoretic tags is determined by the fluorescent tag. The separation of the mixture of fluorescent electrophoretic tags can be carried out by electroseparation, which involves the separation of components in a liquid by application of an electric field, preferably, by electrophoresis (electrokinetic flow) or electroosmotic flow. Electroseparation involves the migration and separation of molecules in an electric field based on differences in mobility. Various forms of electroseparation include by way of example and not limitation, free zone electrophoresis, gel electrophoresis, isoelectric focusing and isotachophoresis. Capillary electroseparation involves electroseparation, preferably by electrokinetic flow, including electrophoretic, dielectrophoretic and/or electroosmotic flow, conducted in a tube or channel of about 1–200 micrometer, usually, about 10–100 micrometers cross-sectional dimensions. The capillary may be a long independent capillary tube or a channel in a wafer or film comprised of silicon, quartz, glass or plastic.

In capillary electroseparation, an aliquot of the reaction mixture containing the cleaved labels is subjected to electroseparation by introducing the aliquot into an electroseparation channel that may be part of, or to, linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

Capillary devices are known for carrying out amplification reactions such as PCR. See, for example, Analytical Chemistry (1996) 68:40 46. Devices are also known that provide functional integration of PCR amplification and capillary electrophoresis in a microfabricated DNA analysis device. One such device is described by Woolley, et al., in *Anal. Chem.* (1996) 68:40814086. The device provides a microfabricated silicon PCR reactor and glass capillary electrophoresis clips. In the device a PCR chamber and a capillary electrophoresis chip are directly linked though a photolithographically fabricated channel filled with a sieving matrix such as hydroxyethylcellulose. Electrophoretic injection directly from the PCR chamber through the cross injection channel is used as an "electrophoretic valve" to couple the PCR and capillary electrophoresis devices on a chip.

The capillary electrophoresis chip contains sufficient number of main or secondary electrophoretic channels to receive the desired number of aliquots from the PCR reaction medium or the solutions containing the cleaved labels, etc., at the intervals chosen.

For capillary electrophoresis one may employ one or more detection zones to detect the separated cleaved labels. It is, of course, within the purview of the present invention to utilize several detection zones depending on the nature of the amplification process, the number of cycles for which a measurement is to be made and so forth. There may be any number of detection zones associated with a single channel or with multiple channels. Suitable detectors for use in the detection zones include, by way of e sample, photomultiplier tubes, photodiodes, photodiode arrays, avalanche photodiodes, linear and array charge coupled device (CCD) chips, CCD camera modules, spectrofluorometers, and the like. Excitation sources include, for example, filtered lamps, LED's, laser diodes, gas, liquid and solid state lasers, and so forth The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. Nos. 5,560,811 (column 11, lines 19–30), 4,675,300, 4,274,240 and 5,324,401, the relevant disclosures of which are incorporated herein by reference.

Those skilled in the electrophoresis arts will recognize a wide range of electric potentials or field strengths may be used, for example, fields of 10 to 1000 V/cm are used with 200–600 V/cm being more typical. The upper voltage limit for commercial systems is 30 kV, with a capillary length of 40–60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from 180 to 1500 nm, usually 220 to 800 nm, more usually 450 to 700 nm, to have low transmission losses. Suitable materials include fused silica, plastics, quartz, glass, and so forth.

The electrophoretic tag may be represented by the formula:

R-L-T wherein R is a fluorescer label, L is a bond or a linking group as described previously, and T comprises a nucleoside base, purine or pyrimidine, and is the base, a nucleoside, nucleotide or nucleotide triphosphate, when the base is retained and is otherwise a functionality resulting from the cleavage.

The number of heteroatoms in L is sufficient to impart the desired charge to the label conjugate, usually from about 1 to about 500, more usually from about 2 to 200, heteroatoms. The atoms in L may be substituted with atoms of the than hydrogen.

The charge-imparting moieties of L may be, for example, amino acids, phosphate diesters, carboxylic acids, thioacids, sulfonic acid, sulfate groups, phosphate monoesters, and the like and combinations of one or more of the above. The number of the above components of L is such as to achieve the desired number of different charge-imparting moieties. The amino acids may be, for example, lysine, aspartic acid, alanine, gamma-aminobutyric acid, glycine, β-alanine, cysteine, glutamic acid, homocysteine, β-alanine and the like. The phosphate diesters include, for example, dimetyl phosphate diester, ethylene glycol linked phosphate diester, and so forth. The thioacids include, by way of example, thioacetic acid, thiopropionic acid, thiobutyric acid and so forth. The carboxylic acids preferably have from 1 to 30 carbon atoms, more preferably, from 2 to 15 carbon atoms and preferably comprise one or more heteroatoms and may be, for example, acetic acid derivatives, formic acid derivatives, succinic acid derivatives, citric acid derivatives, phytic acid derivatives and the like.

Conjugates of particular interest comprise fluorescent compound and a different amino acid or combinations thereof in the form of peptide or combinations of amino acids and thioacids or other carboxylic acids. Such compounds are represented by the formula:

R'-L'-T wherein R' is a fluorescer, L' is an amino acid or peptide or combinations of amino acids and thioacids or other carboxylic acids and T is a functionality for linking to a nucleoside base or is a nucleoside, nucleotide or nucleotide triphosphate.

In a preferred embodiment of the present invention, the charge-imparting moiety is conveniently composed primarily of amino acids but also may include thioacids and other carboxylic acids having from one to six carbon atoms. The charge imparting moiety may have from 1 to 30, preferably 1 to 20, more preferably, 1 to 10 amino acids per moiety and may also comprise 1 to 3 thioacids or other carboxylic acids: As mentioned above, any amino acid, both naturally occurring and synthetic, may be employed.

In a particular embodiment the label conjugates may be represented by the formula:

Fluorescer-L"-(amino acid)$_n$-T"

wherein L" is a bond or a linking group of from 1 to 20 atoms other than hydrogen, n is 1 to 20, and T" comprises a nucleoside base, purine or pyrimidine, including a base, a nucleoside, a nucleotide or nucleotide triphosphate. An example of label conjugates in this embodiment, by way of illustration and not limitation, is one in which the fluorescer is fluorescein, L" is a bond in the form of an amide linkage involving the meta-carboxyl of the fluorescein and the terminal amine at the end of a five-carbon chain diamine, (amino acid) is represented as X, and T" is a nucleotide. These label conjugates may be represented as follows:

Fluorescein-(CO)NH—(CH$_2$)$_5$(X)$_n$T"

Figure 1:
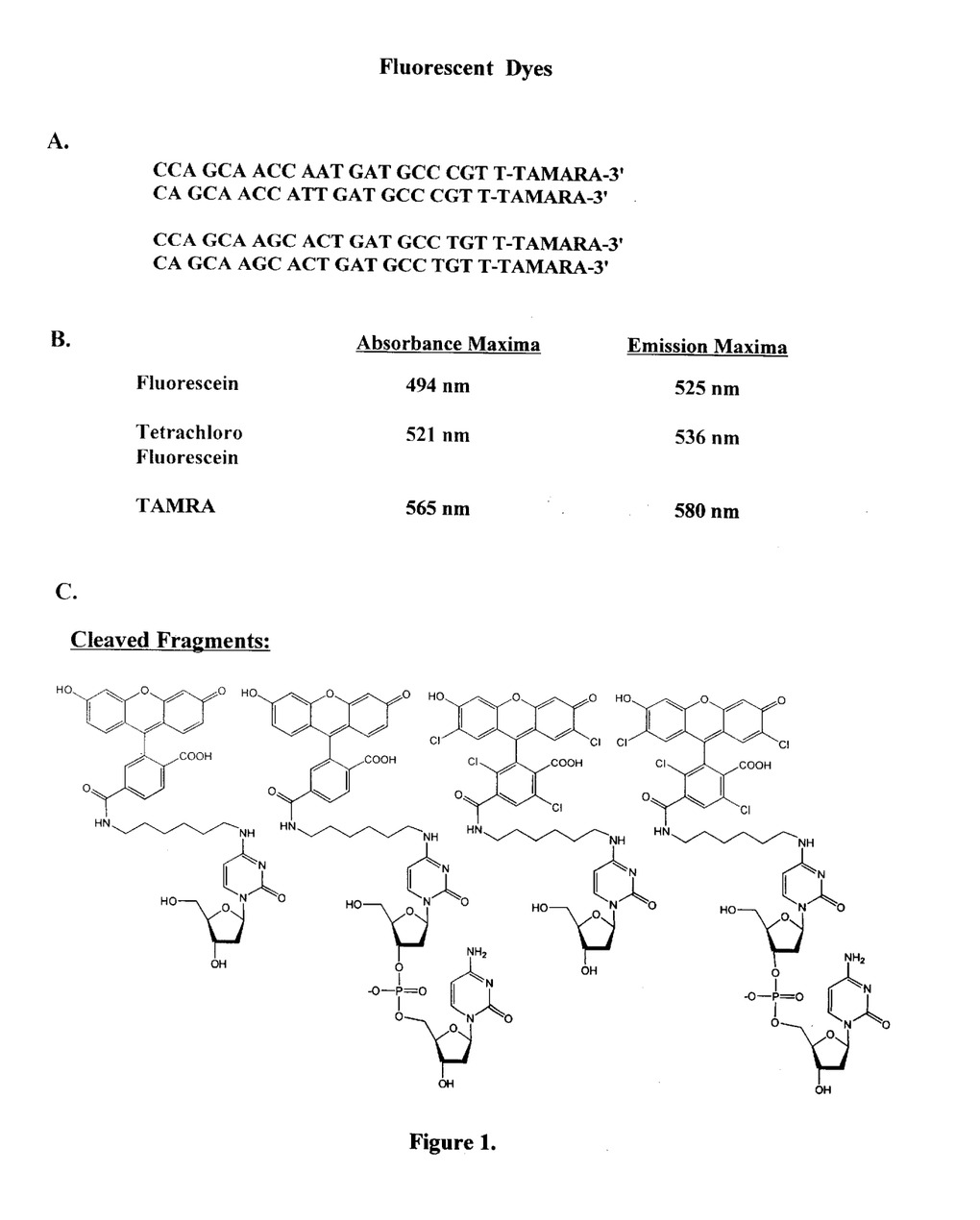

Various characteristics of example label conjugates are shown in Tables 1 and 2, wherein T" is a deoxythymidine, X is as set forth in Table 1, q is charge, M is mass, and mobility is $q/M^{2/3}$. Examples of such label conjugates are shown in FIG. 1C.

TABLE 1

| No. | X | Charge |
|---|---|---|
| 1 | NH | −2 |
| 2 | NH-lysine | −1 |
| 3 | NH-(lysine)$_2$ | neutral |
| 4 | NH-alanine | −3 |
| 5 | NH-aspartic acid | −4 |
| 6 | NH-(aspartic acid)$_2$ | −5 |
| 7 | NH-(aspartic acid)$_3$ | −6 |
| 8 | NH-(aspartic acid)$_4$ | −7 |
| 9 | NH-(aspartic acid)$_5$ | −8 |
| 10 | NH-(aspartic acid)$_6$ | −9 |
| 11 | NH-(aspartic acid)$_7$ | −10 |
| 12 | NH-alanine-lysine | −2 (unique q/M) |
| 13 | NH-aspartic acid-lysine | −3 (unique q/M) |

TABLE 1-continued

| No. | X | Charge |
|---|---|---|
| 14 | NH-(aspartic acid)$_2$-lysine | −4 (unique q/M) |
| 15 | NH-(aspartic acid)$_3$-lysine | −5 (unique q/M) |
| 16 | NH-(aspartic acid)$_4$-lysine | −6 (unique q/M) |
| 17 | NH-(aspartic acid)$_5$-lysine | −7 (unique q/M) |
| 18 | NH-(aspartic acid)$_6$-lysine | −8 (unique q/M) |
| 19 | NH-(aspartic acid)$_7$-lysine | −9 (unique q/M) |
| 20 | NH-(aspartic acid)$_8$-lysine | −10 (unique q/M) |
| 21 | NH-(lysine)$_4$ | +1 |
| 22 | NH-(lysine)$_5$ | +2 |

TABLE 2

| No. | Mass(M) | Charge (q) | M⅔ | q/M⅔ | Mobility |
|---|---|---|---|---|---|
| 1 | 744.82 | 0 | 82.16765 | 0 | 0 |
| 2 | 877.02 | 0 | 91.62336 | 0 | 0 |
| 3 | 828.71 | −1 | 88.22704 | −0.01133 | −0.16546 |
| 4 | 970.71 | −1 | 98.03767 | −0.0102 | −0.1489 |
| 5 | 700.82 | −2 | 78.89891 | −0.02535 | −0.37004 |
| 6 | 842.83 | −2 | 89.22639 | −0.2241 | −0.32721 |
| 7 | 815.92 | −3 | 87.31692 | −0.03436 | −0.50155 |
| 8 | 957.92 | −3 | 97.17461 | −0.03087 | −0.45067 |
| 9 | 931.02 | −4 | 95.34677 | −0.04195 | −0.61242 |
| 10 | 1073.02 | −4 | 104.8106 | −0.03816 | −0.55712 |
| 11 | 1046 | −5 | 103.0436 | −0.04852 | −0.70834 |
| 12 | 1188 | −5 | 112.1702 | −0.04458 | −0.65071 |
| 13 | 1161 | −6 | 110.4642 | −0.05432 | −0.79291 |
| 14 | 1303 | −6 | 119.297 | −0.05029 | −0.7342 |
| 15 | 1276 | −7 | 117.6433 | −0.0595 | −0.86861 |
| 16 | 1418 | −7 | 126.2169 | −0.05546 | −0.80961 |
| 17 | 1391 | −8 | 124.6096 | −0.0642 | −0.9372 |
| 18 | 1533 | −8 | 132.952 | −0.06017 | −0.87839 |
| 19 | 1506 | −9 | 131.3863 | −0.0685 | −0.99997 |
| 20 | 1645 | −9 | 139.6205 | −0.06451 | −0.94167 |
| 21 | 793.52 | 1 | 85.7114 | 0.011667 | 0.170316 |
| 22 | 935.52 | 1 | 95.65376 | 0.010454 | 0.152613 |

The label conjugates may be prepared utilizing conjugating techniques that are well known in the art. The charge-imparting moiety L may be synthesized from smaller molecules that have functional groups that provide for linking of the molecules to one another, usually in a linear chain. Such functional groups include carboxylic acids, amines, and hydroxy- or thiol- groups. In accordance with the present invention the charge-imparting moiety may have one or more side groups pending from the core chain. The side groups have a functionality to provide for linking to a label or to another molecule of the charge-imparting moiety.

Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides contaning sulfur and phosphorus such as, e.g. sulfonate, phosphate esters, sulfonamides, thioesters, etc., and the like, The chemistry for performing the types of syntheses to form the charge-imparting moiety as a peptide chain is well known in the art. See, for example, Marglin, et al., Ann. Rev. Biochem. (1970) 39,841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, J. Am. Chem. Soc. (1980) 85:2149–2154 and Houghten et al., Int. J. Pep. Prot. Res. (1980) 16:311–320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (11969); and J. Meienhofer, "Hormonal Proteins and Peptides", (1973), vol. 2, p 46, Academic Press (New York), for solid phase peptide synthesis and E. Schroder, et al., "The Peptides, vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under condition suitable for forming the amide linkage. The protecting group is then removed from this newly added amino acid residue and the next amino acid (suitably protected) is then added, and go forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may he removed by reduction with hydrogen and palladium on charcoal, sodium in liquid ammonia, etc.; hydrolysis with trifluoroacetic acid, hydrofluoric acid, and the like.

After the synthesis of the peptide is complete the peptide is removed from the resin by conventional means such as ammonolysis, acidolysis and the like. The fully deprotected peptide may then be purified by techniques known in the such as chromatography, for example, adsorption chromatography, ion exchange chromatography, partition chromatography, high performance liquid chromatography, thin layer chromatography, and so forth.

As can be seen, the selected peptide representing a charge-imparting moiety may be synthesized separately and then attached to the label either directly or by means of a linking group. On the other hand, the peptide may be synthesized as a growing chain on the label. In any of the above approaches, the linking of the peptide or amino acid to the label may be carried out using one or more of the techniques described above for the synthesis of peptides or for linking moieties to labels.

The aforementioned label conjugates with different electrophoretic mobility permit a multiplexed amplification and detection of multiple single nucleotide polymorphisms. The label conjugates are linked to oligonucleotides in a manner similar to that for labels in general, by means of linkages that are enzymatically cleavable. It is, of course, within the purview of the present invention to prepare any number of label conjugates for performing multiplexed determinations. Accordingly, for example, with 40 to 50 different label conjugates separated in a single separation channel and 96 different amplification reactions with 96 separation channels on a single plastic chip, one can detect 4000 to 5000single nucleotide polymorphisms.

As exemplary of the subject invention, four target polynucleotides T1, T2, T3 and T4 are employed. Oligonucleotide primers PR1, PR2, PR3 and PR4 are employed, each respectively capable of hybridizing to a sequence in the respective target polynucleotides. Also employed are four oligonucleotide snp detection sequences, PB1, PB2, PB3 and P4. Each of the snp detection sequences comprises a fluorescents label F1, F2, F3 and F4, respectively. In this example, there is a mismatch between PB2 and T2, which comprises a single nucleotide polymorphism The reaction medium comprising the above reagents and nucleoside triphosphates and a template dependent polynucleoitide polymerase having 5' to 3' exonuclease activity is treated under amplification conditions. Primers PR1, PR3, PR3 and PR4 hybridize to their respective target polynucleotides and are extended to yield extended primers EPR1, EPR2, EPR3 and EPR4. snp detection sequences PB1, PB3 and PB4, which hybridize with their respective target polynucleotides, are acted upon by the exonuclease to cleave a single nucleotide bearing the respective fluorescent label, PB2, which does not bind to the target polynucleotide, is not cleaved. Cleaved fragments C1, C3 and C4 are injected into a separation channel in a chip for conducting electroseparation. The labels are identified by their specific mobility and fluorescence upon irradiation. The separated labels are related to the presence and amount of the respective target polynucleotide.

As a matter of convenience, predetermined amounts of reagents employed in the present invention can be provided in a kit in packaged combination. A kit can comprise in packaged combination an oligonucleotide primer for each polynucleotide suspected of being in said set wherein each of said primers is hybridizable to a first sequence of a respective polynucleotide if present, a template dependent polynucleotide polyimerase, nucleoside triphosphates, and a set of oligonucleotide snp detection sequences, each of the snp detection sequences having a fluorescent label at its 5'-end and having a sequence at its 5'-end that is hybridizable to a respective polynucleotide wherein each of the electrophoretic labels is cleavable from the snp detection sequence.

The kit may further comprise a device for conducting capillary electrophoresis as well as a template dependent polynucleotide polymerase having 5' to 3' exonuclease activity. The kit can further include various buffered media, some of which may contain one or more of the above reagents.

The relative amounts of the various reagent in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. For example, the dNTPs, the oligonucleotide pairs optionally the polymerase, may be included in a single container, which may also include an appropriate amount of buffer. The kits may also include a written description of a method in accordance with the present invention as described above.

In one embodiment of the kit, the electrophoretic tags are fluorescent conjugates represented by the formula:

R-L-T"

wherein R is a fluorescer, L is a linking group, as described previously, and $T^a$ is a functionality for binding to a nucleoside base, purine or pyrimidine, or a nucleoside base, a nucleoside, nucleotide or nucleotide triphosphate.

In another embodiment of a kit, the electrophoretic tags are fluorescent conjugates represented by the formula:

R'-L'-T$^b$ wherein R' is a fluorescer, L' is a bond, an amino acid, an amino acid, a peptide, or combinations of amino acids and thioacids or other carboxylic acids, and $T^b$ is a nucleotide or nucleotide triphosphate.

In another embodiment of a kit the electrophoretic tag is a fluorescent conjugate represented by the formula:

Fluorescer-L"-(amino acid)$_n$-T$^c$ wherein L" is a bond or a linking group of from 1 to 20 atoms in the chain and n is 1 to 100. The fluorescer may be fluorescein, the amino acid may be lysine and L" may be a bond in the form of an amide linkage involving the meta-carboxyl of the fluorescein and the terminal amine group of lysine, and $T^c$ is the OH of the carboxyl of the last amino acid, a moiety of from 0 to 6 carbon atoms for linking the carboxy to a nucleoside, nucleotide or nucleotide triphosphate.

In another embodiment of a kit in accordance with the invention, the electrophoretic tag is a label conjugate represented by the formula;

Fluorescein-(CO)NH—(CH$_2$)$_5$—NH—(CO)(X)

wherein X is selected from the group consisting of: OH, NH-lysine, NH-(lysine)$_2$, NH-alanine, NH-aspartic acid, NH-(aspartic acid)$_2$, NH-(aspartic acid)$_3$, NH-(aspartic acid)$_4$, NH-(aspartic acid)$_5$, NH-(aspartic acid)$_6$, NH-(aspartic acid)$_7$, NH-alanine-lysine, NH-aspartic acid-lysine, NH-(aspartic acid)$_2$-lysine, NH-(aspartic acid)$_3$-lysine, NH-(aspartic acid)$_4$-lysine, NH-(aspartic acid)$_5$-lysine, NH-(aspartic acid)$_6$-lysine, NH-(aspartic acid)$_7$-lysine, NH-(aspartic acid)$_8$-lysine, NH-(lysine)$_4$, and NH-(lysine)$_5$. The terminal carboxy may be linked to $T^c$.

The electrophoretic tags described above may terminate in an appropriate functionality for linking to a nucleotide or nucleotide triphosphate or may terminate in such moieties.

EXAMPLES

The invention is demonstrated further by the following illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, oligonucleotides and peptides used in the following examples were prepared by synthesis using an automated synthesizer and were purified by gel electrophoresis or HPLC.

The following abbreviations have the meanings set forth below;

Tris HCl-Tris(hydroxymethyl)aminomethane-HCl (a 10X solution) from Bio Whittaker, Walkersville, Md.
HPLC—high performance liquid chromatography
BSA—bovine serum albumin from Sigma Chemical Company, St. Louis Mo.
EDTA—ethylenediaminetetraacetate from Sigma Chemical Company
bp—base pairs
g—grams
mM—millimolar
TET—tetrachlorofluorescein
FAM—fluorescein
TAMRA—tetramethyl rhodamine
EOF—electroosmotic flow Reagents:
TET and TAMRA were purchased from Perkin Elmer (Foster City, Calif.) as were conjugates of TET, FAM and TAMRA with oligonucleotides.
Master Mix (2x): 20 mM Tris-HCl, 2.0 mM EDTA, pH 8.0 (8% Glycerol),
10 mM MgCl$_2$, dATP 400 μM, dCTP 400 μM, dGTP 400 μM,
dUTP 400 μM, AmpliTaq Gold ® 0.1 U/μl (from Perkin Elmer), Amperase
UNG® 0.02U/μl (from Perkin Elmer)
Probes and Primers: (10x)
Forward Primer: 3.5 μM 5'-TCA CCA CAT CCC AGT G-3'(SEQ ID NO;1)
Reverse Primer 2.0 μM 5'-GAG GGA GGTTTG GCTG-3'(SEQ ID NO:2)
Plasmid Allele 1 Probe: 2.0 μM (200 nM per reaction) 5'TET-CCA GCA ACC AAT GAT GCC CGT T-TAMRA-3'(SEQ MD NO:3)
Plasmid Allele 2 Probe: 2.0 μM (200 nM per reaction) 5'FAM-CCA GCA AGC ACT GAT GCC TGT T-TAMRA-3'(SEQ ID NO:4)
Target DNA:
Plasmid Allele-1:10 fg/μl=approximately 1000 copies/μl
Plasmid Allele-2: 10 fg/μl=approximately 1000 copies/μl

Example 1

The experiment was set up to run in the following fashion (6 samples, a triplcate for Allele-1 and another triplicate for Allele-2)
22 μl of Mastermix
13 μl of probes and primers (both the probes are present)
4.0 μl of Allele-1 or Allele-2
11 μl of buffer (10 mM Tris-HCl, 1 mM EDTA, pH8.0)
The above volumes were added to a PCR tubes and the reaction mixtures were cycled in the following fashion for 40 cycles.
Initial Steps:
The reaction mixtures were kept at 50° C. for 2 minutes for optimal AmpEmse UNG activity. The 10 minute, 95° C. step was required to activate AmiphTaq Gold DNA Polmerase.

Each of the 40 cycles was performed on a Gene Amp ® system 9600thermal cycler (Perkin Elmer) in the following fashion:

| Melt | Anneal/Extend/Cleave |
|---|---|
| 15 seconds | 60 seconds |
| 95° C. | 60° C. |

Figure 2:
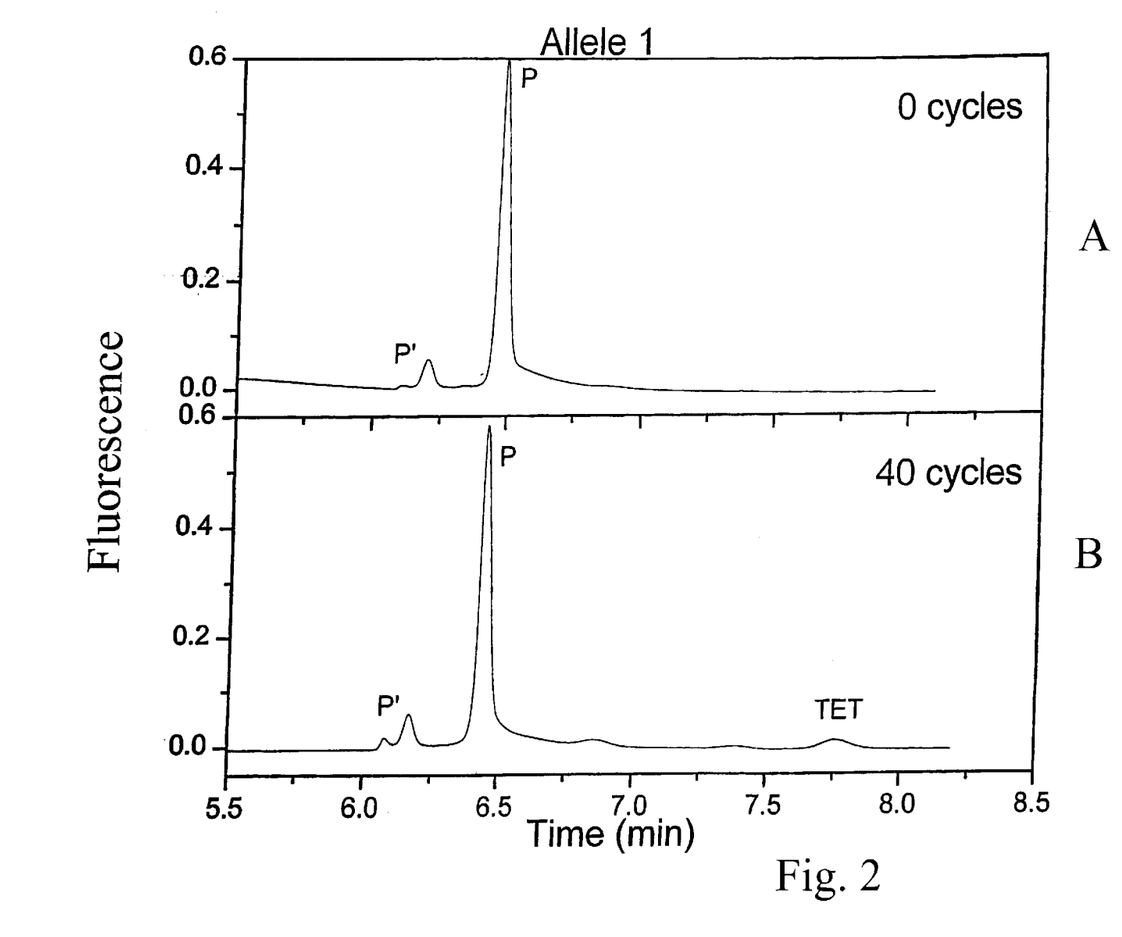

Results from experiments with Allele-1 are shown in FIG. 2. CE separation of the reaction products of Allele 1 after 0 and 40 cycles. CE instent was Beckma P/ACE 5000 with LIF detection. BGE: 2.5% LDD30, 7 M urea,. 1xTBE, Capillary: 100 μm i.d., 375 μm o.d., Lc=27 cm, Ld=6.9 cm. Detection: λex=488 nm, λem=520 nm. Injection: 5 s at 2.0 kV. Field strength: 100 V/cm at room temperature Peaks P=unreacted primer, P'=primer product.

Figure 3:
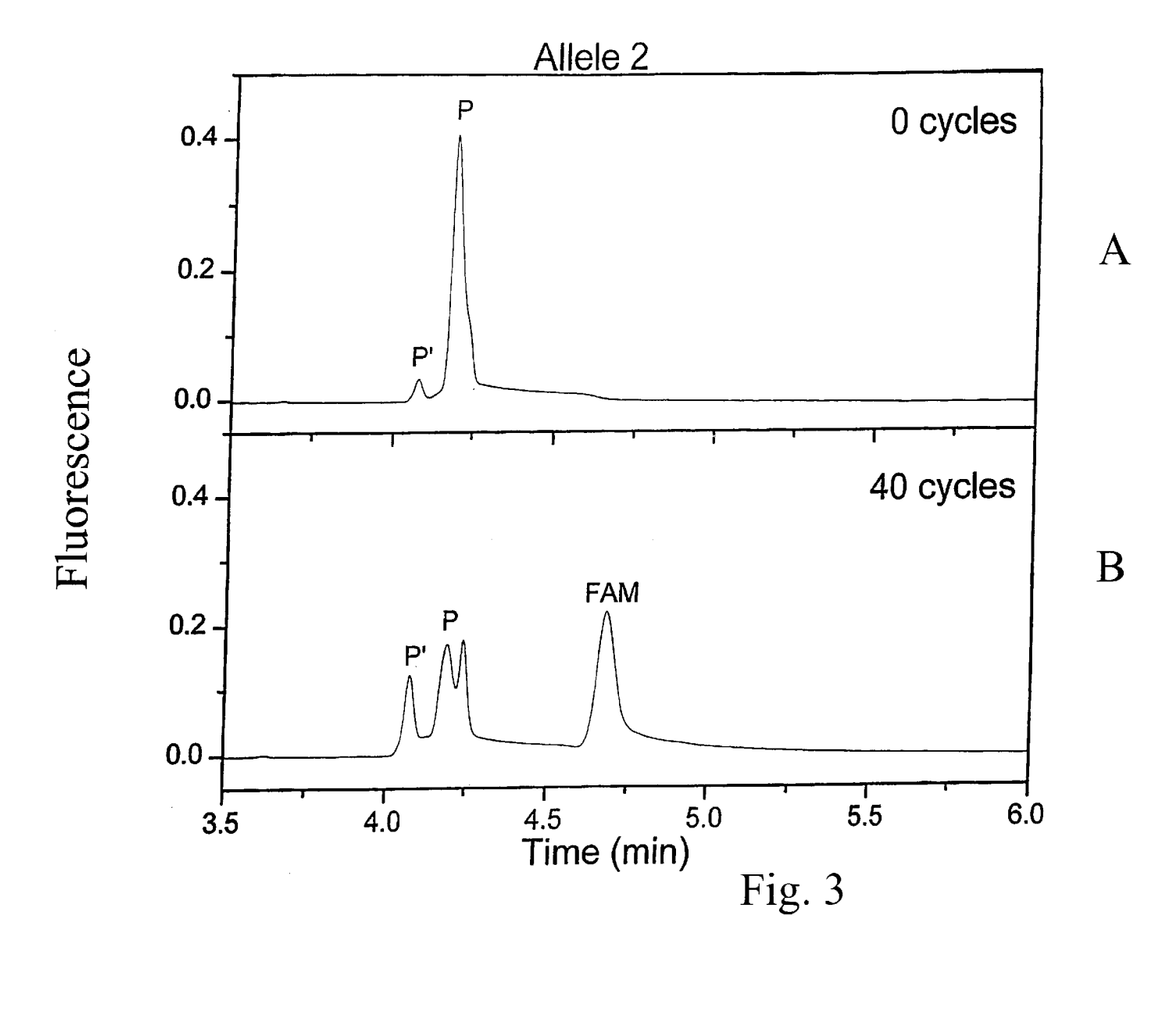

Results from experiments with Allele-2 are shown in FIG. 3. CE separation of the reaction products of Allele 2 after 0 and 40 cycles. Experimental conditions were as given above for FIG. 2 experiment except for BGE composition: 2.0%LDD30, 1xTBE.

Example 2

A Multiplexed Reaction With Both Allele 1 and Allele 2 Present In Equal Ratio The experiment was set up in the following fashion (3 reaction tubes, a triplicate)

22 μl of Mastermix
13 μl of probes and primers (both of the probes were present)
4.0 μl of Allele-1
4.0μl of Allele-2
7μl of buffer (10 mM Tris-HCl, 1 mM EDTA, pH8.0)

The above volumes were added to a PCR tubes and the reaction mixtures were cycled in the following fashion for 40 cycles.

Initial Steps:
The reaction mixtures are kept at 50° C. for 2 minutes for optimal AmpErase UNG activity. The 10 minute, 95° C. step is required to activate AmpliTaq Gold DNA Polymerase.

Each of the 40 cycles is performed in the following fashion

| Melt | Anneal/Extend/Cleave |
|---|---|
| 15 seconds | 60 seconds |
| 95° C. | 60° C. |

Figure 4:
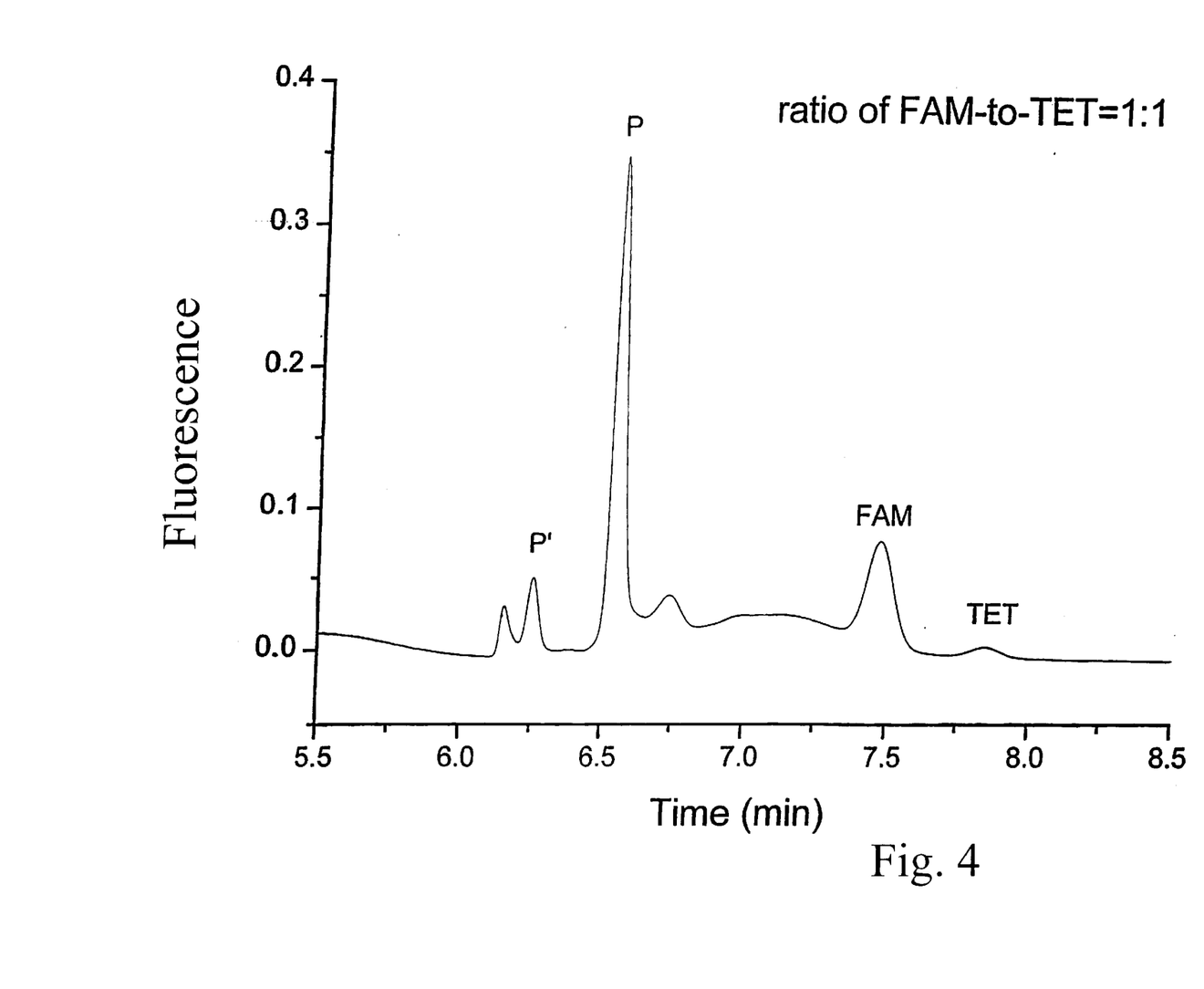
FIG. 4 is a graph of the CE separation of a 1:1 mixture of the 40 cycles products of Alleles 1 and 2, with experimental conditions as described for FIG. 2.

The results are shown in FIG. 4 CE separation of a 1:1 mixture of the 40 cycles products of Alleles 1 and 2. Experimental conditions were as given above for the experiments of FIG. 2.

Example 3

A Multiplexed Reaction With Both Allele 1 and Allele 2: Allele 1 is 10 Times More Concentrated Than Allele 2.

The experiment was set up in the following fashion (3 reaction tubes, a triplicate)

22 μl of Mastermix
13 μl of probes and primers (both the probes were present)
5.0 μl of Allele 1
0.5 μl of Allele 2
9.5 μl of buffer (10 mM Tris-HCl, 11 mM EDTA, pH8.0)

The above volumes were added to respective PCR tubes and the reaction mixtes were cycled in the following fashion for 40 cycles.

Intial Steps:
The reaction mixtures were kept at 50° C. for 2 minutes for optimal AmpErase UNG activity.

The 10 minute 95° C. step was required to activate AmtiTaq Gold DNA Polymerase.

Each of the 40 cycles is performed in the following fashion

| Melt | Anneal/Extend/Cleave |
|---|---|
| 15 seconds | 60 seconds |
| 95° C. | 60° C. |

Figure 5:
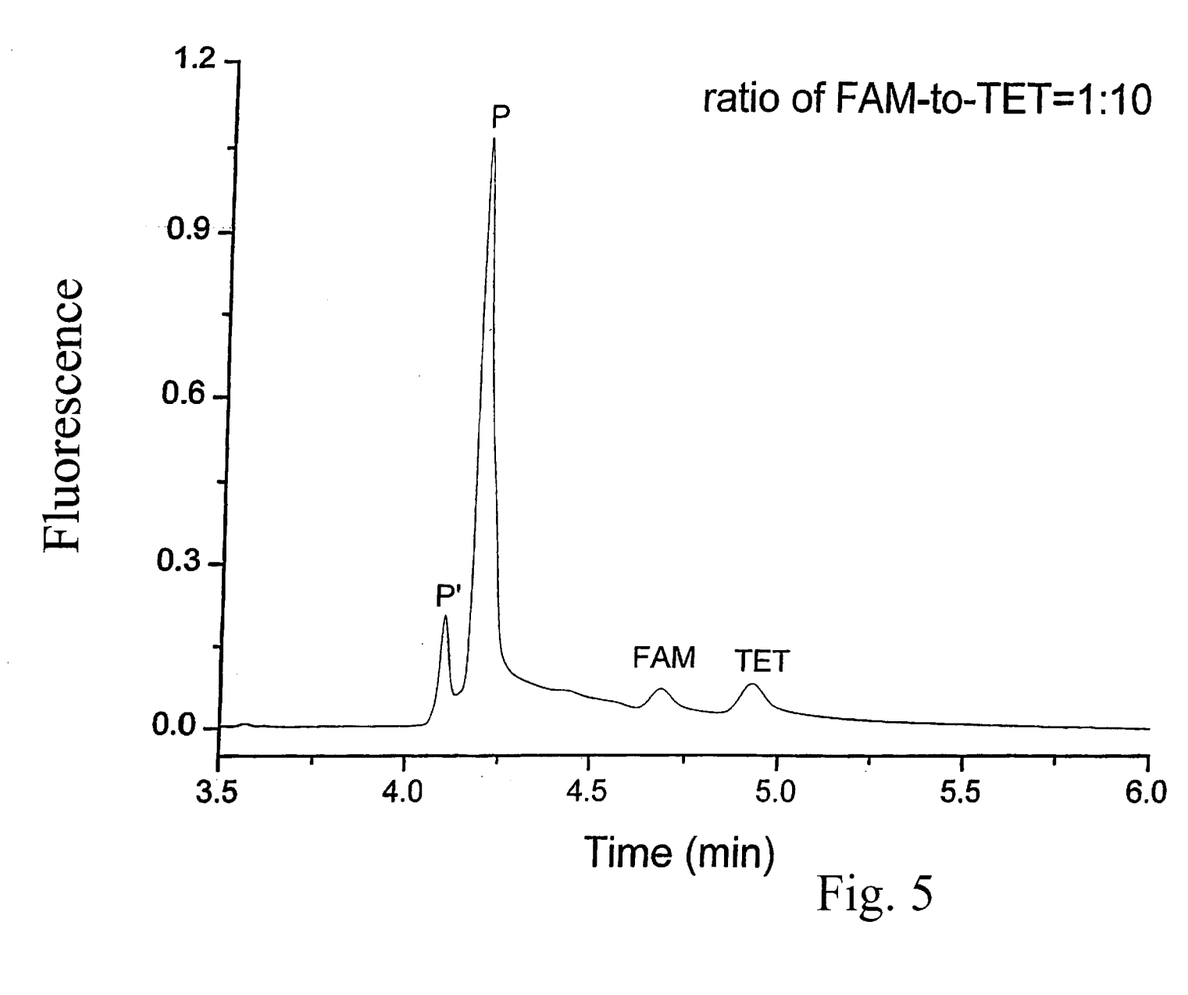
FIG. 5 is a graph of the CE separation of a1:10 mixture of the 40 cycles products of Alleles 1 and 2, with experimental conditions as described for FIG. 2.

The results are shown in FIG. 5. CE separation of a 1:10 mixture of the 40 cycles products of Alleles 1 and 2. Experimental conditions were as given for the ex periments of FIG. 2.

Example 4

Electroseparation of Label Conjugates On Microfluidic Chip

Label conjugates comprising fluorescein linked to three different peptides, namely, KKAA (SEQ ID NO:5), KKKA (SEQ ID NO;6), ad KKKK (SEQ ID NO:7) were prepared as follows: The protected tetrapeptide was prepared on resin using Merrifield reagents. The N-terminus of the last amino acid was reacted with fluorescein N-hydroxysuccinimide (Molecular Probes). The peptides were cleaved from the resin and purified by high performance liquid chromatography (HPLC).

The label conjugates, prepared as described above, and fluorescein were combined in an aqueous buffered solution and were separated and detected in an electrophoresis chip. Detection was 0.5 cm for the injection point on the anodal side of an electrophoresis channel. FITC-KKKK exhibited negative charge and FITC-KKKK and FITC-KKKK exhibited positive charge as determined by the migration time relative to EOF. The net charge of FITC-KKKK was greater than +1 and FITC-KKKA and FITC-KKKK migrated electrophoretically against the EOF.

All publications and patent applications cited in this specification are herein incorporated by reference as if each individual publicaton or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended clams.

What is claimed is:

1. A method for detecting a plurality of single nucleotide polymorphisms (snps) present in a sample of target DNA, said method comprising the steps of:

combining under primer extension conditions, said target DNA and, for each snp in said target DNA to be detected, a pair of oligonucleotides comprising a primer and a snp-specific snp detection sequence, wherein said primer extension conditions comprise a polymerase having 5'-3' exonuclease activity, wherein said primer specifically binds to a first strand of said target DNA and said snp detection sequence also binds to said first strand of said target DNA downstream from said primer in the direction of primer extension and at the site of said snp in said target DNA, and wherein said snp detection sequence comprises (i) an oligonucleotide comprising a base other than the terminal nucleotides that is complementary to one of said plurality of snps in said target DNA and at least one nucleotide linkage resistant to nuclease hydrolysis at a position immediately 3' of the second nucleotide from the 5'-end of said oligonucleotide, and (ii) an electrophoretic tag comprising a linker and a fluorophor, wherein said electrophoretic tag is joined to the 5'-end nucleotide of said oligonucleotide, such that cleavage of the snp-detection sequence at its 5' end by the 5'-3' exonuclease produces a single released fluorescent product composed of the electrophoretic tag and the 5'-end nucleotide of the snp-detection sequence, wherein each said released fluorescent product produced from a given snp detection sequence has a known, unique electrophoretic mobility with respect to the released fluorescent products produced from all other such snp detection sequences, by virtue of a unique charge/mass ratio associated with the electrophoretic tag;

by said combining, producing said single released fluorescent product for each associated snp present in the sample;

separating said released fluorescent products by electrophoresis; and identifying each snp present in said sample by the presence of said single released fluorescent product whose electrophoretic mobility is associated with that snp.

2. A method according to claim 1, wherein said pair have a total of at least 36 nucleotides.

3. The method according to claim 1, wherein said snp detection sequence further comprises a quencher which quenches said fluorophor when said fluorophor is bound to said snp detection sequence, and including the further step of monitoring the change in fluorescence during said executing step.

4. A method according to claim 1, wherein said snp detection sequences are within 200 nucleotides of said primer when bound to said target DNA.

5. A method according to claim 1, wherein said snp detection sequence comprises a charged peptide.

6. A method according to claim 5, wherein said charged peptide comprises at least one of lysine, arginine and histidine.

7. A kit for detecting one or more of a plurality of single nucleotide polymorphisms (snps) that may be present in a sample of target DNA, said kit comprising a plurality of snp detection sequences, wherein each said snp detection sequence comprises:

(i) an oligonucleotide consisting of at least 12 nucleotides, and containing a nucleotide other than the 5' or 3' terminal nucleotides that is complementary to a snp in a target DNA, and at least one nucleotide linkage at positions immediately 3' of the second nucleotide at the 5'-end of said oligonucleotide that is resistant to nuclease hydrolysis; and (ii) a snp-specific electrophoretic tag comprising a linker and a fluorophor, wherein said electrophoretic tag is joined to the 5'-end nucleotide of said oligonucleotide, and wherein cleavage of the snp-detection sequence between the first and second nucleotides at the 5'-end of said oligonucleotide produces a single released fluorescent product composed of the electrophoretic tag and the 5'-end nucleotide of the snp-detection sequence, wherein each said released fluorescent product produced from a given snp detection sequence has a known, unique electrophoretic mobility with respect to the released fluorescent products produced from snp detection sequences specific for other snps, by virtue of a unique charge/mass ratio associated with the electrophoretic tag:

wherein cleavage of a snp detection sequence by a 5'-to-3' exonuclease produces, for each snp detection sequence, a single snp-specific fluorescent product containing a snp-specific electrophoretic tag and the 5' nucleotide of said oliognucleotide.

8. A kit according to claim 7, wherein said electrophoretic tag comprises a fluorophor.

9. The kit according to claim 8, wherein said electrophoretic tag comprises an amino acid or peptide.

10. A kit according to claim 9, wherein said amino acid or said peptide comprises lysine, arginine or histidine.

11. The kit according to claim 7, wherein said electrophoretic tag comprises an amino acid or peptide.

12. The kit according to claim 11, wherein said amino acid or said peptide comprises lysine, arginine or histidine.

* * * * *